United States Patent [19]
Schuette

[11] Patent Number: 5,888,364
[45] Date of Patent: Mar. 30, 1999

[54] GEL ELECTROPHORESIS APPARATUS

[75] Inventor: Michael W. Schuette, Vienna, Va.

[73] Assignee: Life Technologies, Inc., Rockville, Md.

[21] Appl. No.: 816,076

[22] Filed: Mar. 13, 1997

[51] Int. Cl.⁶ .................................................. G01N 27/26
[52] U.S. Cl. ........................ 204/466; 204/467; 204/616; 204/618; 204/621
[58] Field of Search .................................. 204/466, 621; 7/467, 616, 618

[56] References Cited

U.S. PATENT DOCUMENTS

| | | | |
|---|---|---|---|
| 3,129,158 | 4/1964 | Raymond et al. | 204/467 |
| 3,677,930 | 7/1972 | Meshbane et al. | 204/467 |
| 3,989,612 | 11/1976 | Kragt et al. | 204/462 |
| 4,061,561 | 12/1977 | Fletcher et al. | 204/616 |
| 4,142,960 | 3/1979 | Hahn et al. | 204/619 |
| 4,151,065 | 4/1979 | Kaplan et al. | 204/620 |
| 4,194,963 | 3/1980 | Denckla | 204/620 |
| 4,234,400 | 11/1980 | Kaplan et al. | 204/610 |
| 4,284,491 | 8/1981 | Vesterberg | 204/461 |
| 4,292,161 | 9/1981 | Hoefer et al. | 204/606 |
| 4,325,796 | 4/1982 | Hoefer et al. | 204/467 |
| 4,358,358 | 11/1982 | Rhodes | 435/285.2 |
| 4,415,418 | 11/1983 | Turre et al. | 204/466 |
| 4,574,040 | 3/1986 | Delony et al. | 204/606 |
| 4,576,693 | 3/1986 | Kreisher et al. | 264/219 |
| 4,588,491 | 5/1986 | Kreisher et al. | 204/620 |
| 4,624,768 | 11/1986 | Yoshida et al. | 204/616 |
| 4,773,984 | 9/1988 | Fleshner et al. | 204/618 |
| 4,865,715 | 9/1989 | Hellman, Jr. | 204/618 |
| 4,957,613 | 9/1990 | Schuette | 204/618 |
| 5,158,661 | 10/1992 | Hansen | 204/607 |
| 5,736,025 | 4/1998 | Smith et al. | 204/621 |

FOREIGN PATENT DOCUMENTS 8105858  4/1996  Japan .

OTHER PUBLICATIONS

JAPIO abstract of Masaharu et al. (JP08105858 A), Apr. 23, 996.

BioTechniques –The Journal of Laboratory Technology for Bioresearch, vol. 18, No. 3, Mar., 1995, ad reading "Introducing Semi–Automated DNA Sequencing for under $10,000 genomyxLR™ DNA Sequencer..." on Circle Reader Service No. 106.

BioTechniques –The Journal of Laboratory Technology for Bioresearch, vol. 18, No. 6, Jun., 1995, ad reading "GenomyxLR™ DNA Sequencer..." on Circle Reader Service No. 165.

(List continued on next page.)

*Primary Examiner*—Robert Warden
*Assistant Examiner*—Alex Noguerda
*Attorney, Agent, or Firm*—Sterne, Kessler, Goldstein & Fox P.L.L.C.

[57] ABSTRACT

A gel electrophoresis apparatus and a cooling system therefor. The apparatus includes a front panel and a back panel. A gel slab is contained in a gel slab platform between the front and back panels. The gel slab platform extends upwardly to the front edge of an upper buffer reservoir and downwardly to a lower buffer reservoir. A conventional gel mold assembly is inserted into the apparatus and supported by the gel slab platform. A cooling unit is disposed below the lower buffer reservoir of the apparatus. A baffle plate is inserted between the front panel and a back panel of the apparatus. When the cooling unit is actuated, the baffle plate directs a cooling medium through the apparatus and between the front panel and the back panel to cool the gel slab. The apparatus also includes dampers which are pivotally mounted on the apparatus at the top of the baffle plate. The dampers are used to control the flow of the cooling medium through each baffle individually. The apparatus further includes clamps which are pivotally mounted on the sides of the apparatus, and are used to hold the gel mold in place in the gel slab platform during testing. The clamps are designed with a hinge so that they naturally fall away from the gel slab platform when not in use.

22 Claims, 10 Drawing Sheets

OTHER PUBLICATIONS

Excerpt from Bethesda Research Laboratories, Life Technologies, Inc. Catalog entitled "Put a Smile On Your Face, Not on Your Gel With the Model S2" (date unknown).

Excerpt from Hoefer Scientific Instruments Catalog, "Poker Face® Nucleic Acid Sequencer", pp. 34–36. (date unknown).

Excerpt from BioRad Catalog, "Sequi–Gen™ Sequencing System", pp. 244, 247. (date unknown).

Excerpt from LKB Pharmacia Catalog, "Macrophor System", pp. 32–35. (date unknown).

Excerpt from LKB Pharmacia Catalog, "Apparatus for Sequencing", pp. 18, 19 and ordering information. (date unknown).

Excerpt from Hoefer Scientific Instruments catalog entitled, "Poker Face™ II Nucleic Acid Sequencers", month unknown 1992–93, cover pages and pp. 37–40.

Excerpt from Stratagene catalog entitled, "Base Ace® Vertical Sequencing Apparatus", month unknown 1994, cover p. and pages 244–245.

Excerpt from BioRad catalog entitled "Sequi–Gen GT Sequencing Cell", month unknown 1997, cover pages and pp. 194–196.

Excerpt from Pharmacia Biotech Catalog, entitled "Hoefer SQ3 Sequencer", month unknown 1997, cover pages and pp. 316–317.

GEL ELECTROPHORESIS APPARATUS

FIELD OF THE INVENTION

This invention relates to an apparatus for performing gel electrophoresis. In particular, this invention relates to a cooling system, including cooling channels disposed on the gel electrophoresis apparatus, for maintaining an even temperature distribution over a gel slab disposed therein.

BACKGROUND OF THE INVENTION

Electrophoresis is based on the principle that charged particles suspended between opposite poles and in an electric field migrate toward the pole possessing the charge opposite that of the particle. The extent of migration is an indication of the composition of the particles. Electrophoretic separation is often used to separate DNA or RNA fragments generated as part of nucleic acid sequencing procedures.

A conventional apparatus for performing electrophoresis is described in detail in U.S. Pat. No. 4,773,984 to Flesher et al., the disclosure of which is incorporated herein by reference. A typical apparatus includes a gel mold composed of two flat glass plates separated by thin spacers placed at opposite edges. A polyacrylamide gel slab is cast between these plates. The electrophoretic separation will be carried out in this gel slab. Some apparatus are designed to orient the gel vertically; others are designed to orient the gel horizontally. A vertical orientation has generally been found to be preferred for the electrophoresis of nucleic acids in such applications as nucleic acid sequencing. A support platform having means for securing the gel mold to the support platform supports the gel mold.

The apparatus also has two reservoirs for containing a buffer solution, one installed toward the upper end of the support platform and a second installed toward the lower end of the support platform. An electrode is installed in each reservoir to apply a voltage to the buffer solution in each reservoir. These electrodes are typically made from platinum. However, platinum electrodes are costly and must be replaced frequently because the electrodes become brittle after several uses. Thus, what is needed is an electrode that would be a sufficient conductor of electricity and be less fragile and less costly than conventional platinum electrodes.

Placement of the gel mold against the support platform situates the gel slab so that when buffer solution is added to each of the reservoirs, an effective electrical contact is established between the buffer solution in one reservoir and the buffer solution in the other reservoir through the gel slab. Thus, most of the voltage differential between the electrodes occurs within the gel slab. Conventional electrophoretic separation is performed by applying between 1500 and 1800 volts, approximately 60 Watts, of electricity to the buffer solution and the gel slab. This involves a pre-run time, for heating the unit, of twenty to thirty minutes and a nominal run time, for completing electrophoresis, of eighty to eighty-five minutes.

When electrophoretic separation is performed, substantial heat is generated in the gel slab. Typically, the heat is removed by placing a large conducting plate in contact with the gel mold. Often this conducting plate is incorporated as part of the support platform against which the gel mold is placed. Means are provided for securing the gel mold against the conducting plate once it has been inserted into the support platform.

The process of performing electrophoretic separation includes: casting a gel slab in the gel mold, preheating the gel mold in the electrophoresis apparatus, inserting samples into the gel slab, applying electricity across the gel slab to perform electrophoretic separation, and removing the gel mold from the apparatus for developing the gel slab. This process is lengthy, often taking two full days to complete testing of a single gel slab. One method available to accelerate the preheating and testing stages of the process is to increase the voltage across the gel slab. However, an increase in voltage causes excess heat to build up in the gel slab, causing hot spots. The resulting variation in temperature across the gel slab can cause the samples to separate through the gel at different rates, thereby causing a "smile" or "frown" shape in the resulting bands. These distortions make comparison of the resulting bands difficult. Further, the hot spots present a danger to the samples because severe temperature fluctuations may destroy a sample.

The conventional conductive plate is insufficient to dissipate heat from the gel slab when the voltage is significantly increased. Thus, a cooling system is needed that will dissipate heat from the gel slab during accelerated electrophoretic separation and that will maintain the gel at a constant and evenly distributed temperature across the gel slab.

SUMMARY OF THE INVENTION

The present invention relates to a vertical gel electrophoresis apparatus and a cooling system therefor. The apparatus includes a front panel and a second front panel which define therebetween a substantially vertical gel slab platform. The apparatus also includes a back panel so that a gel slab is contained between the front panel and the back panel. The gel slab platform extends upwardly to the front edge of an upper buffer reservoir and downwardly to a lower buffer reservoir. Electrodes are placed in each buffer reservoir. A conventional gel mold assembly is inserted into the apparatus and supported by the gel slab platform. Placement of the gel mold against the support platform situates the gel slab so that when buffer solution is added to each of the reservoirs, an effective electrical contact is established between the buffer solution in the upper buffer reservoir and the buffer solution in the lower buffer reservoir through the gel slab. Thus, most of the voltage differential between the electrodes occurs within the gel slab.

During use, substantial heat may build up in the gel slab and cause aberrant test results. As such, a cooling unit, including a fan or a pump, is fluidly connected to the apparatus. This cooling unit directs a cooling medium, such as air or a cooling fluid, past the gel slab to dissipate heat from the gel slab. At least one baffle plate is inserted between the front panel and the back panel of the apparatus. When the cooling unit is actuated, the baffle plate directs the cooling medium through a channel or channels in the apparatus formed between the front panel and the back panel to cool the gel slab. There may be a single baffle or many baffles in the baffle plate. The baffles can be all of equal size or of varying sizes to address certain areas of overheating in the gel slab. The apparatus also includes a damper or dampers which are pivotally mounted on the apparatus at the top of each baffle of the baffle plate. The dampers are used to control the amount of cooling medium flowing through each baffle individually, and can be opened or closed to address areas of overheating in the gel slab.

The cooling system of the present invention, including the cooling unit and baffle plate, provide sufficient cooling of the gel slab to enable the user to operate with between 2500 and 2800 volts, approximately 130–135 Watts, of electricity across the buffer solution and the gel slab. Thus, the present invention significantly reduces the pre-run time to ten minutes and the nominal run time to forty-five to fifty minutes.

The present invention further includes clamps which are pivotally mounted on the sides of the apparatus. These clamps are used to hold the gel mold in place in the gel slab platform during the electrophoresis process. The clamps are designed with a hinge so that they naturally fall away from the gel slab platform when not in use. As such, the user can easily insert or extract the gel mold into or from the gel slab platform. Further, the clamps are designed so that it takes only one hand to fasten and unfasten the clamps.

BRIEF DESCRIPTION OF THE FIGURES

The foregoing and other features and advantages of the invention will be apparent from the following, more particular description of a preferred embodiment of the invention, as illustrated in the accompanying drawings.

DETAILED DESCRIPTION OF THE PREFERRED EMBODIMENT

Figure 1:
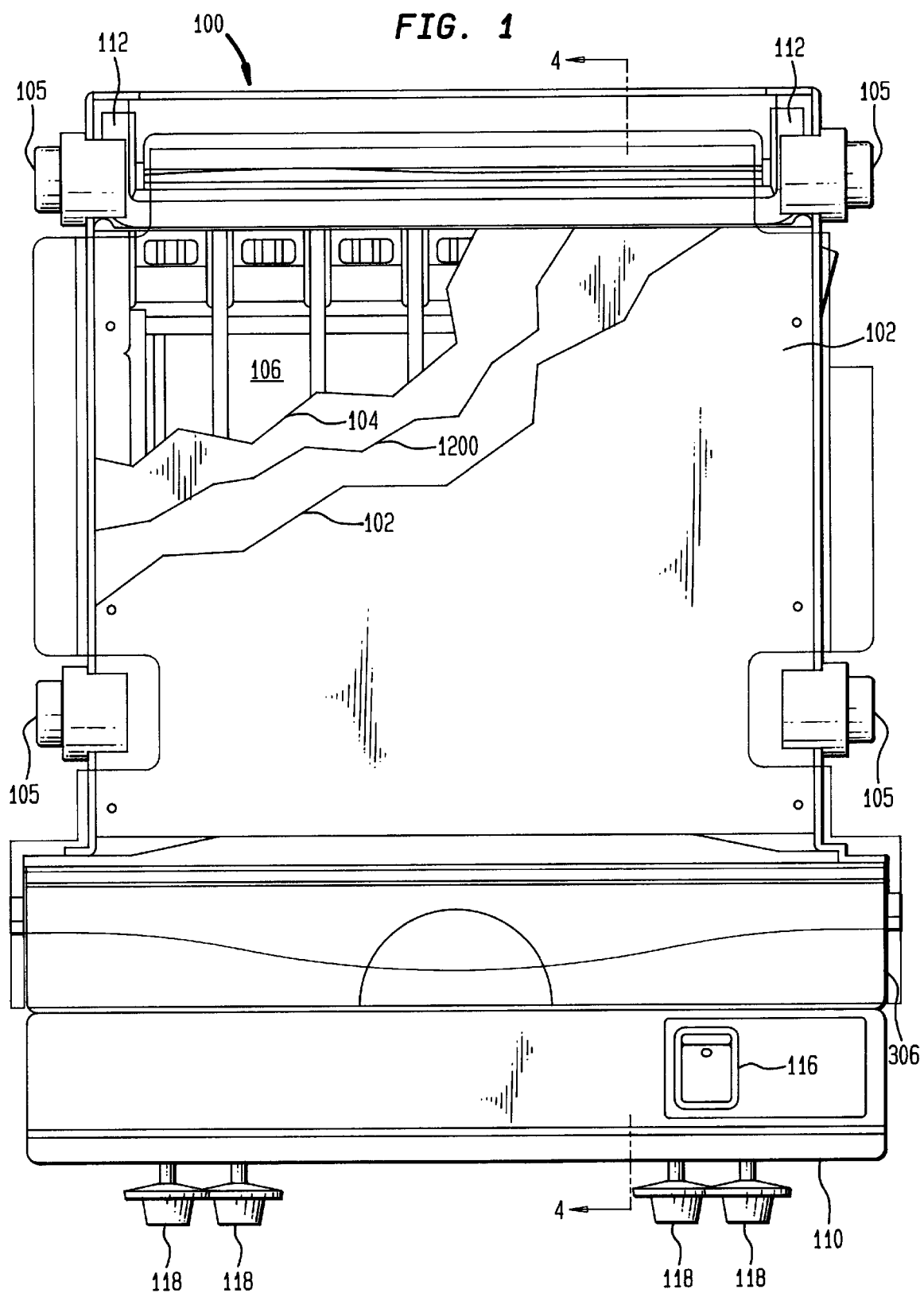
FIG. 1 shows a front, partially cut-away plan view of an electrophoresis apparatus and cooling unit of the present invention.

A preferred embodiment of the present invention is now described with reference to the figures where like reference numbers indicate identical or functionally similar elements. While specific configurations and arrangements are discussed, it should be understood that this is done for illustrative purposes only. A person skilled in the relevant art will recognize that other configurations and arrangements can be used without departing from the spirit and scope of the invention. It will be apparent to a person skilled in the relevant art that this invention can also be employed in a variety of other devices and applications.

Referring to FIGS. 1–4, a gel electrophoresis apparatus 100 of the present invention is shown having a front panel 102, a back panel 202, vertical left and right side panels 302 (left side panel not shown) and a bottom panel 402. Front panel 102, back panel 202 and bottom panel 402 are joined (fastened or made integral) in any conventional fashion to vertical left and right side panels 302 to form an upright device or frame.

In the preferred embodiment of the present invention, a second front panel 104 is located adjacent front panel 102 and a gel slab platform is defined therebetween. The gel slab platform extends upwardly to the front edge of an upper buffer reservoir 304 and downwardly to a lower buffer reservoir 306. In one embodiment of the invention, lower buffer reservoir 306 is a removable tray (not shown) that is placed in use between frontward projecting extensions of left and right side panels 302. In another embodiment, lower buffer reservoir 306 is made integral with apparatus 100.

Figure 14:
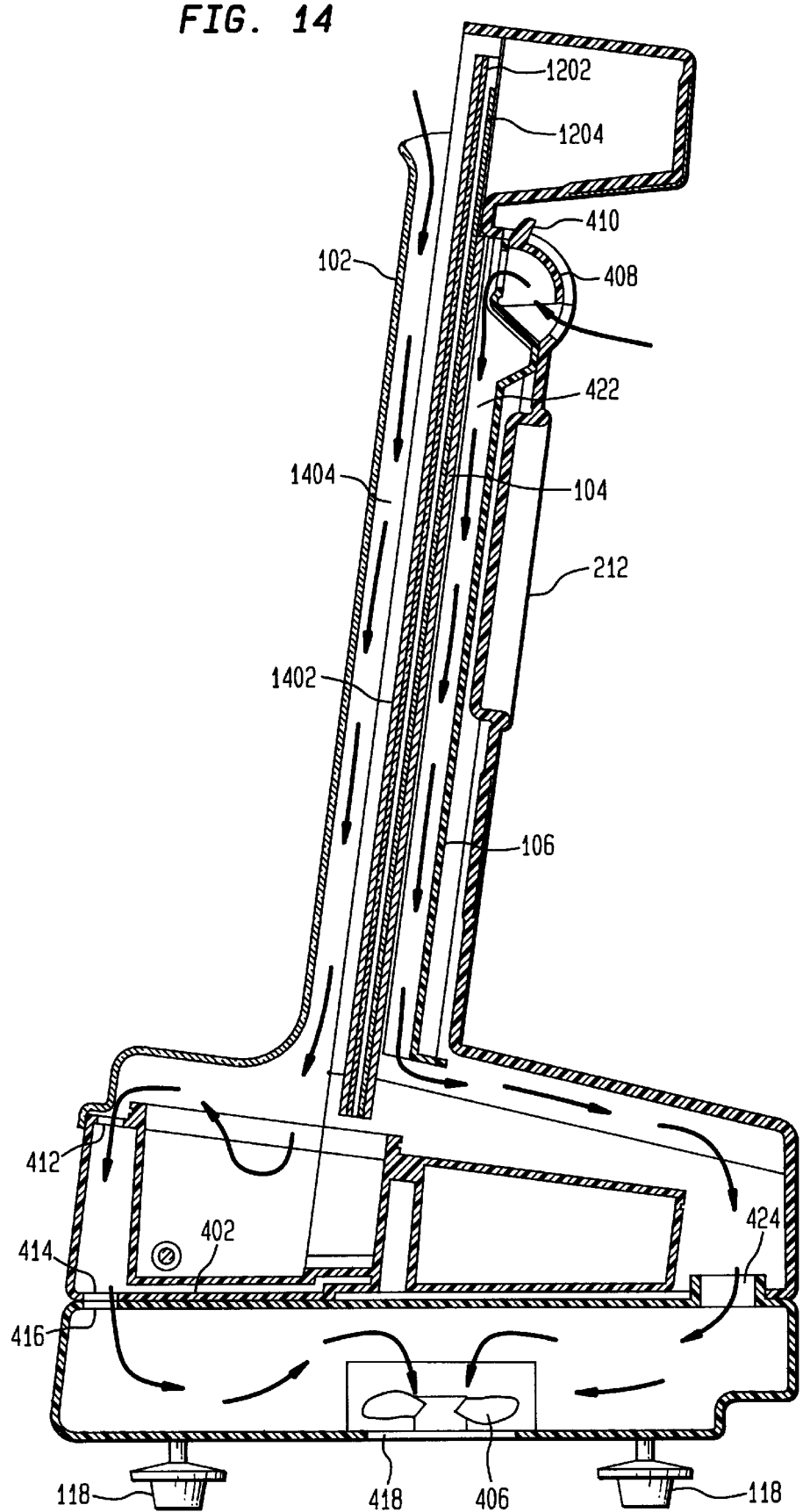
FIG. 14 shows a sectional side view of an alternate embodiment of an electrophoresis apparatus and cooling unit of the present invention.

In a typical electrophoresis experiment, heat is generated within the gel contained with the gel slab. It is desirable to efficiently dissipate this heat across the face of the present invention as defined by front panel 102. In order to effectively dissipate this heat, it is preferred that the second front panel 104 is a good thermal conductor, and may be made of metal, although any of numerous non-metallic materials could be used. Usage of a non-ferrous metal lends itself to easy maintenance and long-life due to lack of oxidation. Additionally, a second conductor plate 1402, as shown in FIG. 14, could be disposed behind front panel 102 and in contact with a front surface of the gel slab to further dissipate heat therein. Second conductor plate 1402, similar to second front panel 104 is made from a good thermal conductor, such as aluminum.

Figure 2:
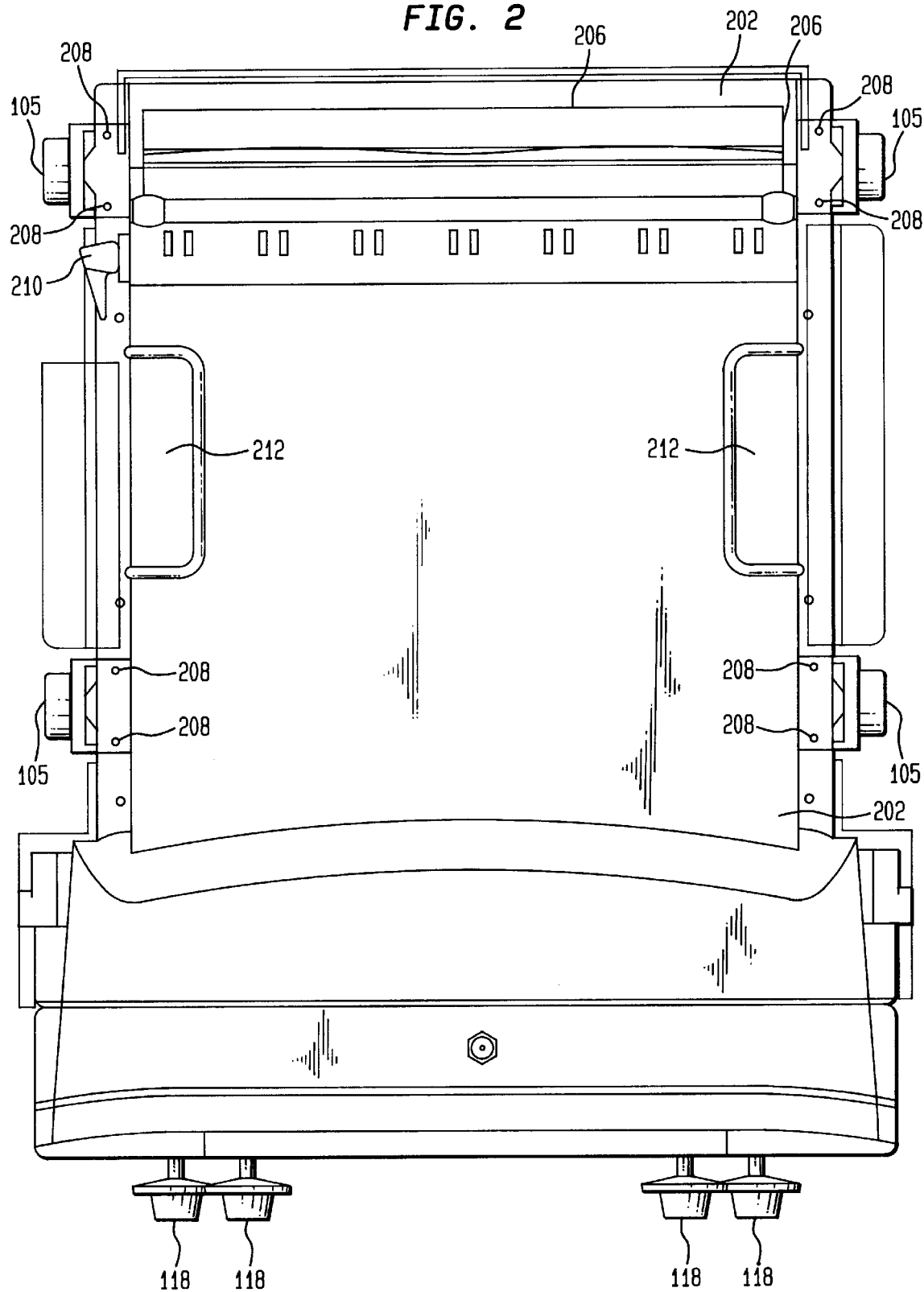
FIG. 2 shows a rear plan view of the electrophoresis apparatus and cooling unit shown in FIG. 1.

As seen best in FIGS. 1–4, upper buffer reservoir 304 is defined in part by back panel 202 having a transparent window 206, an upper buffer reservoir floor 404, a seal gasket 112, a U-shaped front piece (not shown) and the inside surfaces of top portions of the left and right vertical side panels 302. Buffer solution may be drained from upper buffer reservoir 304 via a tube (not shown) and emptied into a portion of lower buffer reservoir 306. Drainage is regulated by a lever 210. As shown in FIG. 2, lever 210 is in a down or off position. This position clamps the drainage tube to prevent buffer solution from draining from upper buffer reservoir 304. In the up or on position, lever 210 disengages from the drainage tube to allow the buffer solution to freely flow out of upper buffer reservoir 304.

Figure 12:
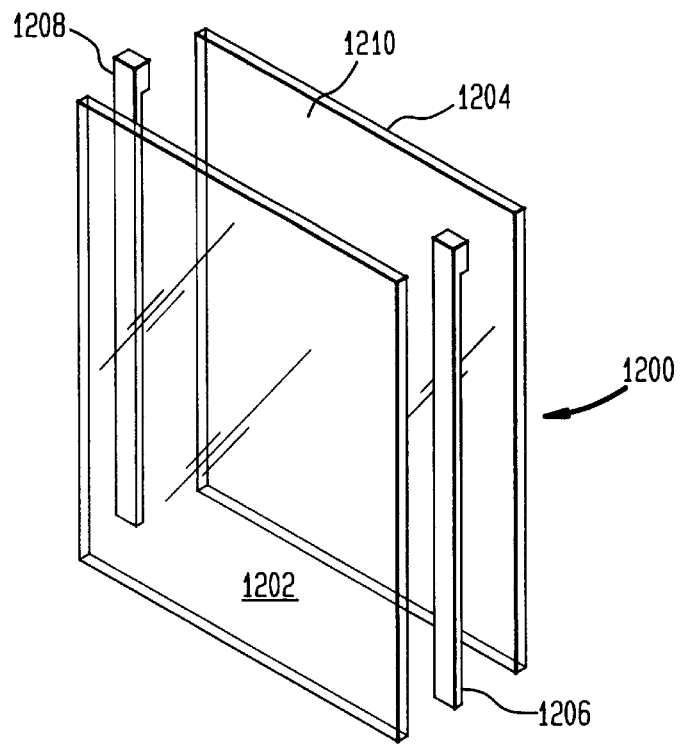
FIG. 12 shows an exploded view of a gel mold assembly.

A conventional gel mold assembly 1200, as shown in FIG. 12, consisting of a first glass plate 1202 and a second glass plate 1204 and spacer gaskets 1206 and 1208 placed therebetween, is placed against second front panel 104 and between upper buffer reservoir 304 and lower buffer reservoir 306. When the first and second glass plates 1202 and 1204 are brought together in a planar fashion with spacer gaskets 1206 and 1208 therebetween, a horizontal gap 1210 the same thickness as the spacer gaskets is formed. A gel slab (not shown) is molded in horizontal gap 1210 so that the desired electrophoretic action can occur therein. The electrophoretic action is caused by the application of an electrical potential (not shown) to the upper and lower buffer solutions causing an electrical differential across the gel slab.

Figure 3:
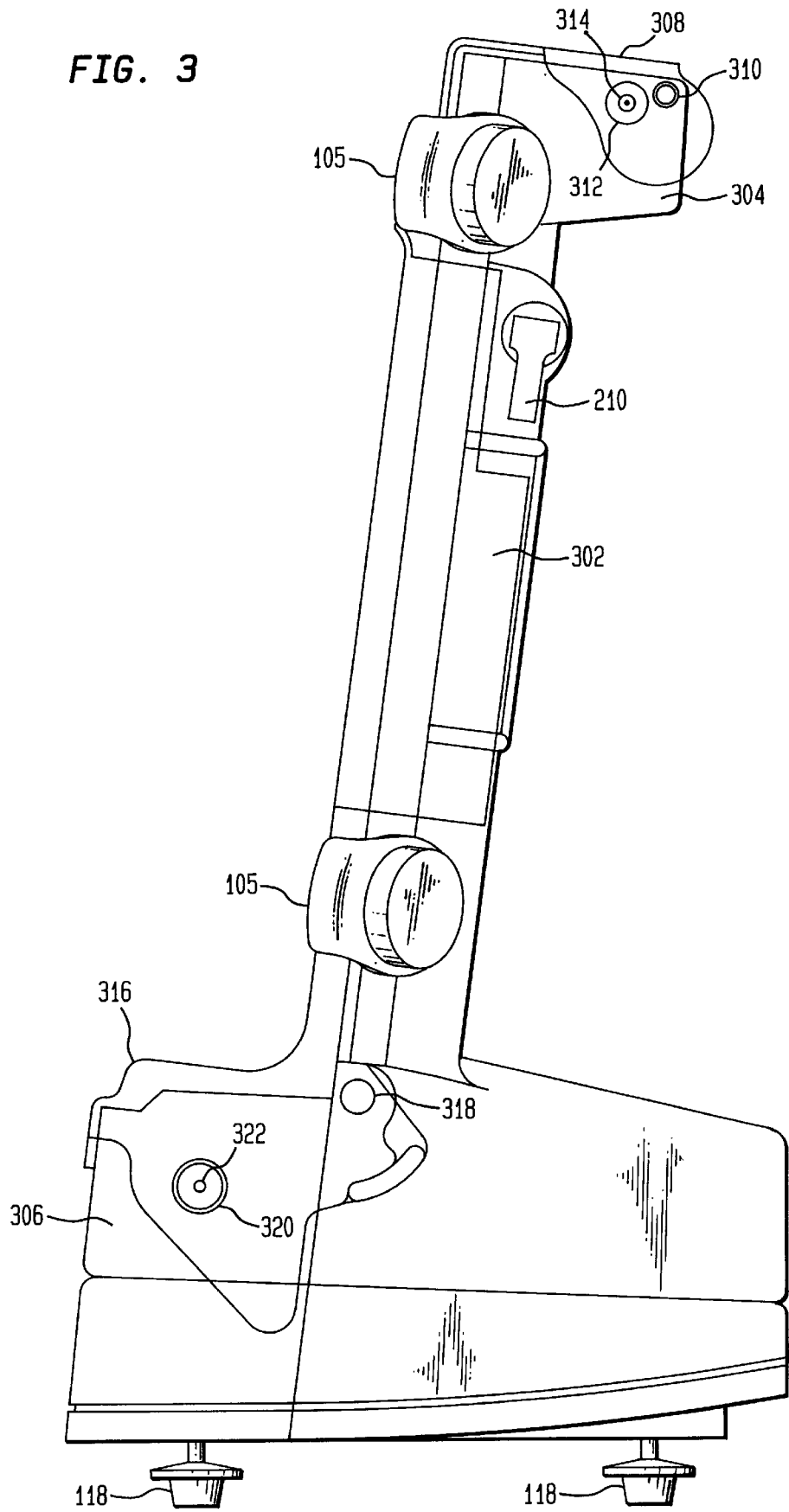
FIG. 3 shows side plan view of the electrophoresis apparatus and cooling unit shown in FIG. 1.

It can be appreciated that in a typical electrophoresis experiment very high electrical potentials are used, requiring great care and awareness by the user and those individuals in the vicinity of the experiment. In order to prevent both electrical shock and buffer solution spillage or contamination, upper buffer reservoir 304 is maintained closed or inaccessible during use by a hinged top closure panel 308. Hinged top closure panel 308 is rotatably attached to upper hinge pins 310 fastened to side panels 302 so that top closure panel 308 can rotate between a first or open position (not shown) to a second or closed position, as shown in FIG. 3. The present invention eliminates electrical shock hazards by provision of a restrictive electrical connection that can be attained only when the top closure panel 308 is in the closed position which obstructs access to the buffer solution in the upper buffer reservoir 304.

Figure 13:
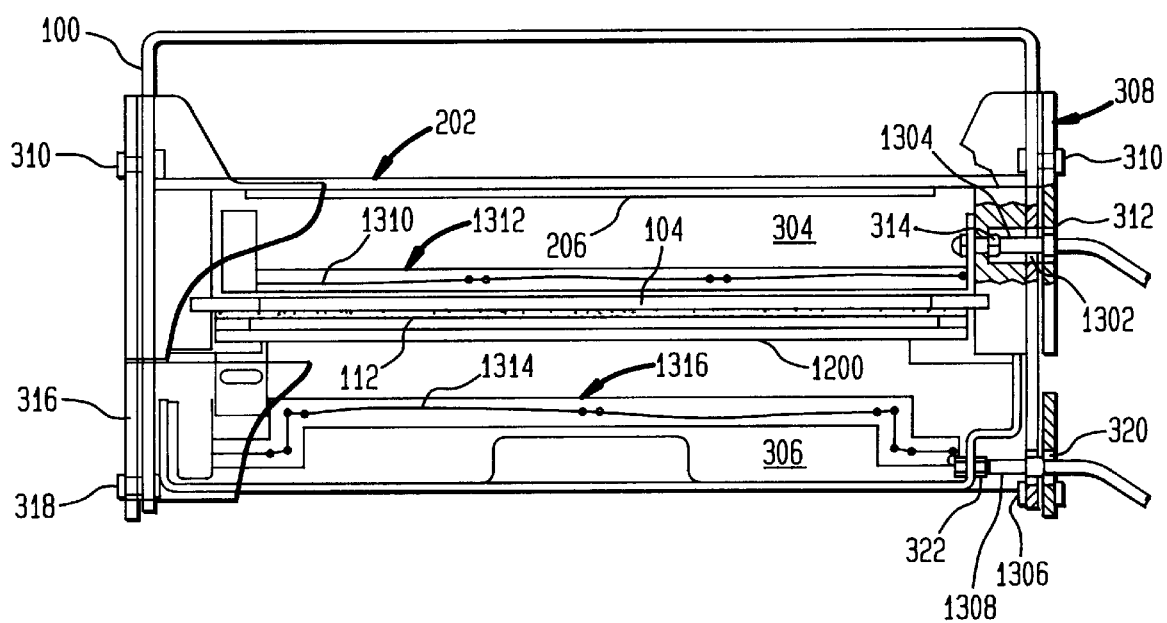
FIG. 13 shows a top, partially cut-away view of the electrophoresis apparatus shown in FIG. 1.

Specifically, hinged top closure panel 308 has a hole 312 formed in the right side panel of top closure panel 308, as shown in FIGS. 3 and 13. A recess 1302, including an upper electrical connector 1304, is formed in an upper portion of right side panel 302 for receiving a banana plug 314. The alignment of hole 312 and recess 1302 occurs only when the top closure panel 308 is in the closed position. Thus, banana plug 314 that provides electricity to apparatus 100 can only be plugged into electrical connector 1304 when top closure panel 308 of upper buffer reservoir 304 is closed. Further, as shown in FIG. 13, the electrical connection between electrical connector 1304 and banana plug 314 physically prevents the rotation of top closure panel 308 from the closed position. Thus, the user cannot be shocked by contact with the buffer solution in upper buffer reservoir 304 since electrical power can only be applied when top closure panel 308 is in the closed position. Further, top closure panel 308 in the closed position prevents contamination of the buffer solution contained in upper buffer reservoir 304.

Similarly, lower buffer reservoir 306 has a hinged bottom closure panel 316 with an electrical interlock to prevent both electrical shock and buffer solution spillage or contamination. Hinged bottom closure panel 316 is rotatably attached to lower hinge pins 318 fastened to side panels 302 so that bottom closure panel 316 can rotate between a first or open position (not shown) to a second or closed position, as shown in FIG. 3. Specifically, hinged bottom closure panel 316 has a hole 320 formed in the right side panel of bottom closure panel 316, as shown in FIG. 3. A recess 1306, including a lower electrical connector 1308, is formed in a lower portion of right side panel 302 for receiving a banana plug 322. The alignment of hole 320 and recess 1306 occurs only when the bottom closure panel 316 is in the closed position. Thus, banana plug 322 that provides electricity to apparatus 100 can only be plugged into electrical connector 1306 when bottom closure panel 316 of lower buffer reservoir 306 is closed. Further, the electrical connection between electrical connector 1308 and banana plug 322 physically prevents the rotation of bottom closure panel 316 from the closed position. Thus, the user cannot be shocked by contact with the buffer solution in lower buffer reservoir 306 since electrical power can only be applied when bottom closure panel 316 is in the closed position. Further, bottom closure panel 316 in the closed position prevents contamination of the buffer solution contained in lower buffer reservoir 306.

In the preferred embodiment, upper buffer reservoir 304 has a stainless steel electrode 1310, which is electrically attached to banana plug 314. However, any noncorroding metallic element such as gold, platinum, rhodium or palladium may be utilized as an electrode in the present invention. Electrode 1310 is looped through holes provided in an L-shaped mounting strip 1312. L-shaped mounting strip 1312 maintains electrode 1310 in the desired position in upper buffer reservoir 304.

In the preferred embodiment, lower buffer reservoir 306 has a titanium electrode 1314 which is sputter coated with platinum, and electrically attached to banana plug 322. However, any noncorroding metallic element such as gold, platinum, rhodium or palladium may be utilized as an electrode in the present invention. Electrode 1314 is looped through holes provided in an L-shaped mounting strip 1316. L-shaped mounting strip 1316 maintains electrode 1314 in the desired position in lower buffer reservoir 306.

Figure 4:
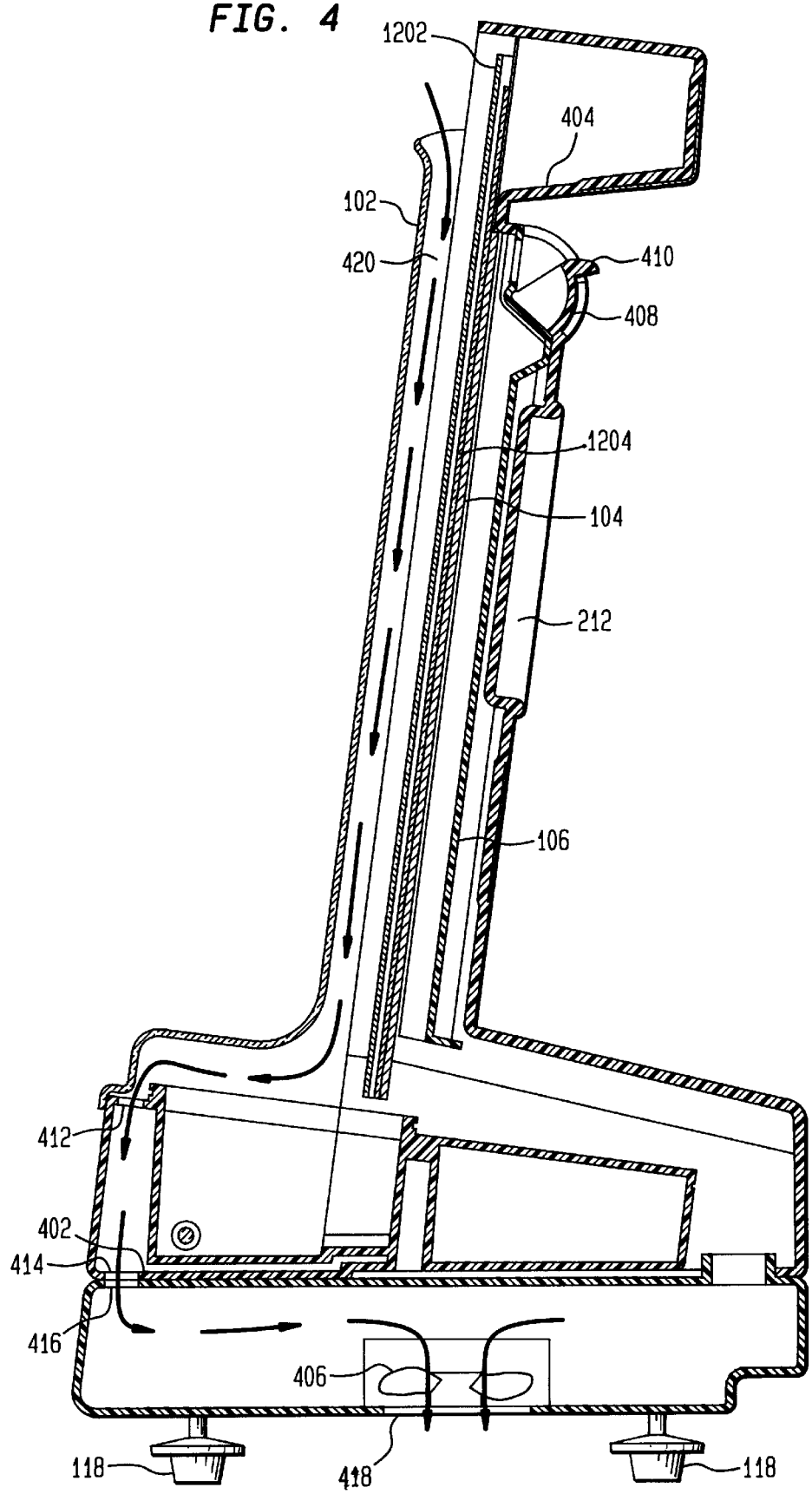
FIG. 4 shows a sectional side view of the electrophoresis apparatus and cooling unit taken along a line 4—4 of FIG. 1.
Figure 5:
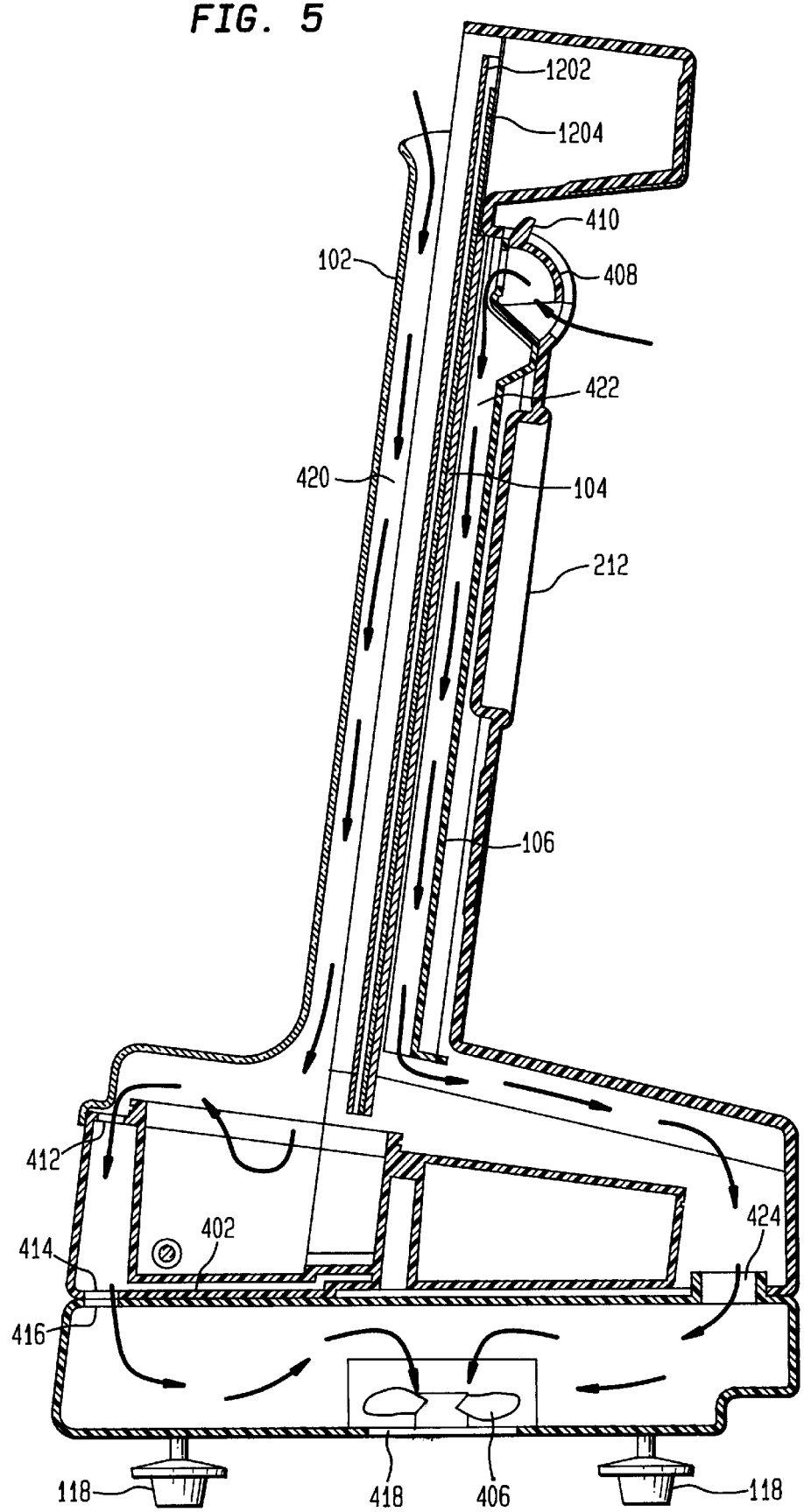
FIG. 5 shows a second sectional side view of the electrophoresis apparatus and cooling unit taken along line 4—4 of FIG. 1.
Figure 6:
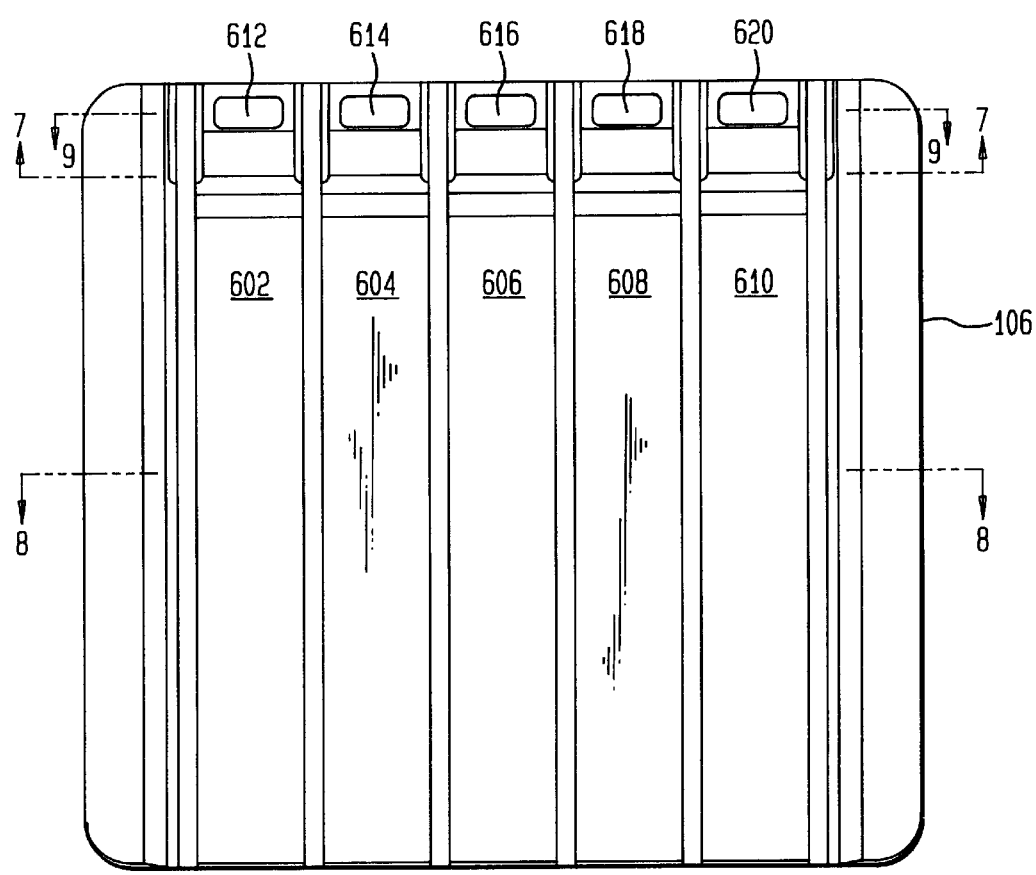
FIG. 6 shows a front plan view of a baffle plate of the present invention.
Figure 7:
FIG. 7 shows a sectional bottom view of the baffle plate taken along a line 7—7 of FIG. 6.
Figure 8:
FIG. 8 shows a sectional top view of the baffle plate taken along a line 8—8 of FIG. 6.
Figure 9:
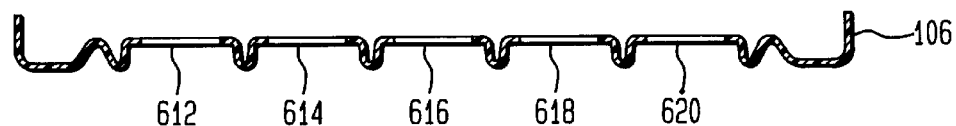
FIG. 9 shows a sectional top view of the baffle plate taken along a line 9—9 of FIG. 6.

Referring to FIGS. 1, 4 and 5, a cooling unit 110 is shown disposed below lower buffer reservoir 306 of apparatus 100. However, the location of cooling unit 110 is not critical to the invention. For example, apparatus 100 could be designed so that cooling unit 110 is disposed above upper buffer reservoir 304. Alternatively, cooling unit 110 could be housed independently of apparatus 100 and connected by a flow means, such as a hollow tube, to the channels in apparatus 100.

In the embodiment shown in FIG. 1, cooling unit 110 houses a fan 406. However, cooling unit 110 may instead house a pump (not shown) for pumping a cooling liquid through apparatus 100. Similarly, cooling unit 110 may be designed to house any other means, such as a vacuum, for transferring a cooling medium through apparatus 100, as would be apparent to one skilled in the relevant art. As shown in FIG. 1, a power switch 116 for fan 406 is disposed on the exterior of cooling unit 110. Fan 406 preferably a 12 Volt, 0.19 Ampere fan, such as Model JF0825B1H made by Jamicon, Taiwan. In an alternate embodiment, two fans could be disposed in cooling unit 110 to provide additional air flow through apparatus 100.

Figure 11A:
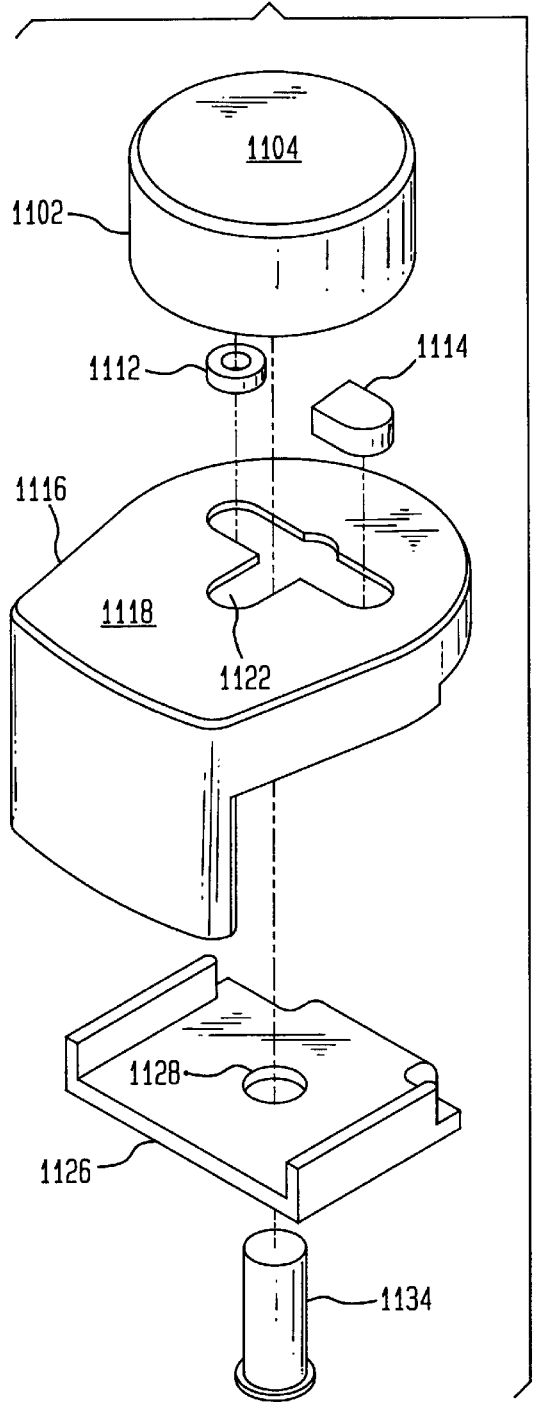
FIG. 11A shows an exploded top perspective view of a knob of the present invention.
Figure 11B:
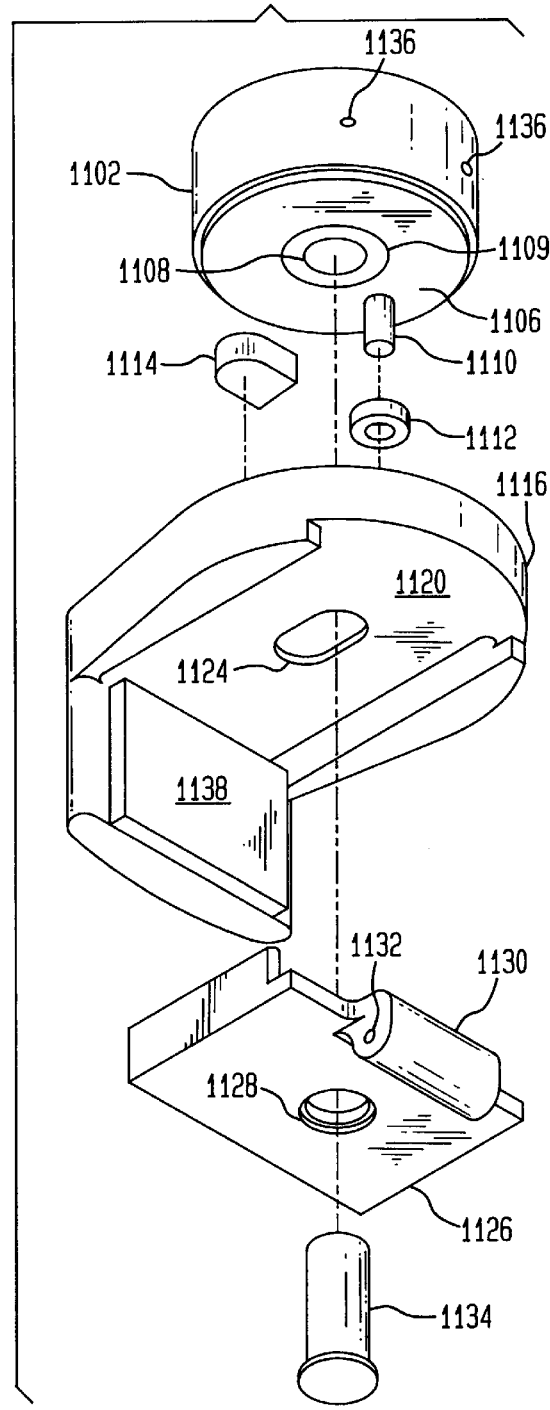
FIG. 11B shows an exploded bottom perspective view of the knob shown in FIG. 11A.

Apparatus 100 also includes clamps 105, shown in more detail in FIGS. 11A and 11B. Clamp 105 is used to clamp gel mold assembly 1200 onto the gel slab platform of apparatus 100. A conventional electrophoresis apparatus uses clamps that have a tendency to fall into the path of gel mold assembly 1200 during insertion of the gel mold into the apparatus. Thus, during insertion of gel mold assembly 1200 into a conventional apparatus, the user must hold the gel mold in one hand and move all the clamps out of the way in order to insert the gel mold adjacent the front panel of the assembly. Clamps 105 of the present invention are hinged so that when not in use, they naturally rotate away from the path of insertion of the gel mold assembly due to gravity. Thus, the user can easily place the gel mold next to second front panel 104 and hold gel mold assembly 1200 in place with one hand, while using a free hand to fasten each clamp 105.

With reference to FIGS. 11A and 11B, each clamp 105 includes a knob 1102 having a top side 1104 and a bottom side 1106. In one embodiment, knob 1102 is formed from injection-molded plastic. A hole 1108 is formed in bottom side 1106. Hole 1108 is lined with a brass insert 1109. A pin 1110 is pressed in place in bottom side 1106 of knob 1102. Knob 1102 is universal, that is, it is designed to rotate both clockwise and counterclockwise to serve as both a left and right-side part for apparatus 100.

Knob 1102 is mounted on an L-shaped platform 1116, having a top surface 1118 and a bottom surface 1120. A T-shaped groove 1122 is formed in top surface 1118 of platform 1116. A corresponding oblong hole 1124 is formed in bottom surface 1120 and extends through platform 1116. A pad 1138 is disposed on one portion of bottom surface 1120 of platform 1116.

Clamp 105 further includes a roller 1112 having a hole formed therein to receive one end of pin 1110. Roller 1112 is disposed in groove 1122 of platform 1116, and is designed to reduce friction as knob 1102 is rotated. A stop 1114 is disposed in groove 1122 opposite roller 1112.

Clamp 105 also includes a mounting plate 1126, having a hole 1128 formed therethrough. Mounting plate 1126 includes a hinge 1130 having a hole 1132 formed therethrough for receiving a pin (not shown). As shown in FIG. 2, hinge 1130 is inserted into a recess (not shown) formed in left and right side panels 302. A pin is then inserted through holes 208 in side panels 302 and through corresponding hole 1132 of hinge 1130 to hingedly attached clamp 105 to assembly 100.

To assemble clamp 105, a pin 1134 is inserted through hole 1128 of hinge portion 1130. Pin 1134 is also inserted through hole 1124 of L-shaped platform 1116 and inserted into hole 1108 of knob 1102. Set screws (not shown) are inserted into holes 1136 of knob 1102 to retain pin 1134 in place. Knob 1102 is designed to spin on pin 1134.

To open clamp 105, the user rotates knob 1102. The rotation of knob 1102 is translated into a lateral open/close movement as pin 1110 and roller 1112 travel along groove 1122. The movement of pin 1110 and roller 1112 is restricted by stop 1114. Depending on how clamp 105 is assembled (i.e., whether stop 1114 is inserted to the right or the left of the center of T-shaped groove 1122, the clamp may be used on the right or left side of apparatus 100. Rotation of knob 1102 also causes L-shaped platform 1116 to slide forward along oblong hole 1124 and rotate outwardly about hinge 1130. FIG. 3 shows clamps 105 on right side panel 302 in an open position, having rotated outwardly and away from gel mold assembly 1200 and front panel 102 of apparatus 100.

In a closed position, pad 1138 disposed on bottom surface 1120 of L-shaped platform 1116 is pressed against gel mold assembly 1200. In one embodiment, pad 1138 is made from a soft rubber material. However, pad 1138 could also be made from any relatively soft material, as would be apparent to one skilled in the relevant art.

As shown in FIG. 3, the gel slab platform of apparatus 100 is tilted so that it is not completely vertical. In this case, the gel slab platform is substantially vertical. The term "substantially vertical" means that the gel slab platform is oriented less than 90 degrees from vertical. More preferably, "substantially vertical" means that the gel slab is oriented less than 45 degrees from vertical. Still more preferably, "substantially vertical" refers to less than 25 degrees from vertical. Still more preferably, "substantially vertical" refers to less than 10 degrees from vertical.

In the embodiment shown in FIG. 3, the gel slab platform of apparatus 100 is tilted approximately 3½ degrees from vertical. This slight tilt shifts the center of gravity of apparatus 100 so that it is less likely to tip over when in use. However, it would be apparent to one skilled in the relevant art to change the tilt of the gel slab platform to shift the center of gravity to accommodate all shapes and sizes of gel electrophoresis devices.

As shown in a cut-away portion of FIG. 1, apparatus 100 includes a baffle plate 106 inserted between second front panel 104 and back panel 202. Baffle plate 106 in combination with cooling unit 110, prevents overheating of gel mold assembly 1200 and the samples deposited therein during electrophoretic separation.

Referring now to FIGS. 6–9, baffle plate 106 is shown in more detail. Baffle plate 106 is used to direct the flow of air from cooling unit 110 through apparatus 100. Baffle plate 106 includes five baffles 602, 604, 606, 608 and 610, each having a separate hole 612, 614, 616, 618 and 620 formed in a top portion therein. It would be apparent to one skilled in the relevant art to use as few or as many baffles as necessary to sufficiently cool the gel slab. For example, in an alternate embodiment, baffle plate 106 could include only a single baffle.

In one embodiment, baffles 602–610 are all equal in size to allow equal amounts of the cooling medium to flow therethrough. However, in an alternate embodiment, baffles 602–610 could be of varying sizes to more efficiently address certain areas of overheating. For example, a greater amount of distortion due to overheating often occurs in the center of the gel slab. Thus, baffles 604, 606, and 608 could be increased in size to accommodate a larger flow of the cooling medium for faster cooling down the center of the gel slab.

Figure 10A:
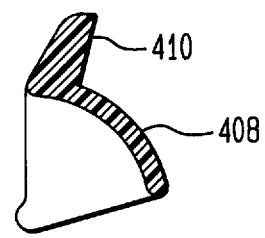
FIG. 10A shows a sectional side view of a damper of the present invention taken along line 10A—10A of the present invention.
Figure 10B:
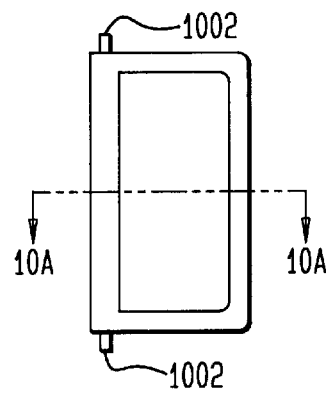
FIG. 10B shows a bottom view of the damper of FIG. 10A.
Figure 10C:
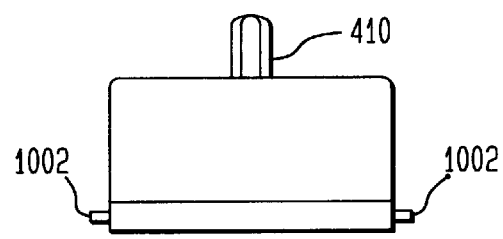
FIG. 10C shows a top view of the damper of FIG. 10A.

Referring now to FIGS. 4 and 5, the flow of the cooling medium through apparatus 100 is shown in a cross-sectional view. Only one of a row of dampers 408 is shown in this view. Generally, each baffle in baffle plate 106 has a corresponding damper 408. Each damper 408, shown in more detail in FIGS. 10A–10C, has a lever 410 which can be used to rotate damper 408 between an open and closed position. Damper 408 rotates about trunnions 1002. Trunnions 1002 are pivotally mounted in apparatus 100 at the top of baffle plate 106 and behind holes 612–620. Baffle plate 106 and damper 408 are shown disposed behind the gel slab in apparatus 100. However, it would be apparent to one skilled in the relevant art that baffle plate 106 and/or damper 408 could also be disposed in front of the gel slab, in addition to or in lieu of the baffle plate and damper disposed behind the gel slab.

In FIG. 4, damper 408 is shown in a closed position. Thus, the cooling medium (represented by arrows in the Figures) propagated by cooling unit 110 flows downwardly through a first channel 420 formed between front panel 102 and first glass plate 1202 of gel mold assembly 1200. Thus, heat produced by the flow of electricity through the gel slab will be dissipated through first glass plate 1202 via the flow of the cooling medium past the gel slab. Heat in the gel slab will also be conducted through second glass plate 1204 and second front panel 104. As the cooling medium travels downwardly through apparatus 100, it passes in front of first glass plate 1202 and through a set of holes 412 (only one hole 412 shown in cross-section view) formed in front of lower buffer reservoir 306. A second set of holes 414 are formed in bottom panel 402 of apparatus 100 for allowing the cooling medium to flow into cooling unit 110. A corresponding set of holes 416 are formed in a top surface of cooling unit 110, so that when apparatus 100 is placed on top of cooling unit 110, holes 414 and 416 align. The cooling medium then exits cooling unit 110 via a vent 418 disposed on a bottom surface of cooling unit 110 below fan 406.

Damper 408 is shown in FIG. 5 in an open position. In this case, the cooling medium flows downwardly in front of first glass plate 1202 of gel mold assembly 1200 to cool the gel slab. Further, the cooling medium flows downwardly behind second front panel 104 to cool the conductive plate and thereby cool the gel slab. The cooling medium flows in front of first glass plate 1202 via first channel 420, as described above with respect to FIG. 4. The cooling medium flows into apparatus 100 via one of holes 612–620 in baffle plate 106, and downwardly through a second channel 422 formed between baffle plate 106 and second front panel 104. The cooling medium then flows out of apparatus 100 through a hole 424 formed in cooling unit 110 and exits via vent 418 beneath fan 406.

As shown in FIG. 14, in an alternate embodiment of the present invention, the cooling medium propogated by cooling unit 110 flows downwardly in front of second conductor plate 1402 and behind second front panel 104 to cool the gel slab. The cooling medium flows in front of second conductor plate 1402 via first channel 1404, formed between front panel 102 and second conductor plate 1402. The cooling medium then flows through holes 412 formed in front of lower buffer reservoir 306 and through corresponding holes 414 and 416. The cooling medium then exits cooling unit 110 via a vent 418 disposed on a bottom surface of cooling unit 110 below fan 406.

The cooling medium flows into apparatus 100 via one of holes 612–620 in baffle plate 106, and downwardly through second channel 422. The cooling medium then flows out of apparatus 100 through hole 424 formed in cooling unit 110 and exits via vent 418 beneath fan 406.

As shown in FIG. 1, cooling unit 110 further includes feet 118, which may be adjustable so as to balance or level apparatus 100 on a table or work surface. Further, apparatus 100 has indentations or handles 212 (shown in FIG. 2) along back panel 106 on either side thereof for accommodating a user's hands to aid in transporting and adjusting the device.

The cooling system of the present invention, including cooling unit 110 and baffle plate 106, provide sufficient cooling of the gel slab to enable the user to place between 2500 and 2800 volts, approximately 130–135 Watts, of electricity across the buffer solution and the gel slab. Thus, the present invention significantly reduces the pre-run time to ten minutes and the nominal run time to forty-five to fifty minutes.

While the invention has been particularly shown and described with reference to preferred embodiments thereof, it will be understood by those skilled in the art that various changes in form and details may be made therein without departing from the spirit and scope of the invention.

What is claimed is:

1. A gel slab electrophoresis apparatus, comprising:
    a substantially vertical gel slab platform having a front panel and a back panel and containing therebetween a gel slab, wherein a first flow channel is formed between said front panel and the gel slab and a second flow channel is formed between the gel slab and the back panel of said apparatus;
    a first buffer reservoir located adjacent a first end of said gel slab platform is adapted to maintain a first buffer solution in effective electrical contact with a first end of the gel slab contained in said gel slab platform;
    a second buffer reservoir located adjacent a second end of said gel slab platform is adapted to maintain a second buffer solution in effective electrical contact with a second end of the gel slab contained in said gel slab platform, whereby an electrical potential may be applied across the gel slab contained within said gel slab platform; and
    a cooling unit for passing a cooling medium through said first flow channel and said second flow channel to cool the gel slab within said gel slab platform;
    wherein the apparatus is constructed so as to non-uniformly distribute said cooling medium across said gel slab.

2. The electrophoresis apparatus of claim 1, wherein said cooling medium is selected from the group comprised of air or a liquid coolant.

3. The electrophoresis apparatus of claim 2, wherein said cooling medium is air.

4. The electrophoresis apparatus of claim 1, wherein said substantially vertical gel slab platform is disposed at an angle of less than 25 degrees from vertical.

5. The electrophoresis apparatus of claim 1, further comprising a second front panel in close contact with the gel slab, wherein said second front panel is located between the gel slab and said back panel.

6. The electrophoresis apparatus of claim 5, wherein said second front panel is a conducting plate for dissipating heat from the gel slab.

7. The electrophoresis apparatus of claim 6, wherein said conducting plate is made from aluminum.

8. The electrophoresis apparatus of claim 6, further comprising:
    a second conducting plate disposed in close contact with the gel slab, wherein said second conducting plate is disposed between said front panel and the gel slab.

9. The electrophoresis apparatus of claim 8, further comprising:
    a baffle plate disposed in at least one of said flow channels, said baffle plate having one or more baffles to direct the flow of said cooling medium through said flow channels.

10. The electrophoresis apparatus of claim 8, further comprising:
    a damper disposed in at least one of said flow channels for controlling the flow of said cooling medium through said flow channels formed in said apparatus.

11. The electrophoresis apparatus of claim 10, wherein said damper comprises a plurality of dampers.

12. The electrophoresis apparatus of claim 9, further comprising:
    a damper disposed in said baffle of said baffle plate for controlling the flow of said cooling medium through said flow channels formed in said apparatus.

13. The electrophoresis apparatus of claim 12, wherein said damper comprises a plurality of dampers.

14. The electrophoresis apparatus of claim 8, wherein said second conducting plate is made from aluminum.

15. The electrophoresis apparatus of claim 1, further comprising:
    a baffle plate disposed in at least one of said flow channels, said baffle plate having one or more baffles to direct the flow of said cooling medium through said flow channels.

16. The electrophoresis apparatus of claim 15, further comprising:
    a damper disposed in said baffle of said baffle plate for controlling the flow of said cooling medium through said flow channels formed in said apparatus.

17. The electrophoresis apparatus of claim 16, wherein said damper comprises a plurality of dampers.

18. The electrophoresis apparatus of claim 1, further comprising:
    a damper disposed in at least one of said flow channels for controlling the flow of said cooling medium through said flow channels formed in said apparatus.

19. A method for performing electrophoretic separation of nucleic acid molecules, comprising the steps of:
    (a) obtaining the apparatus of claim 1;
    (b) applying a sample containing a nucleic acid to be separated to the gel slab; and
    (c) applying electricity across the gel slab.

20. A gel slab electrophoresis apparatus comprising:

a substantially vertical gel slab platform having a front panel and a back panel and containing therebetween a gel slab, wherein a first flow channel is formed between said front panel and the gel slab and a second flow channel is formed between the gel slab and the back panel of said apparatus;

a first buffer reservoir located adjacent a first end of said gel slab platform is adapted to maintain a first buffer solution in effective electrical contact with a first end of the gel slab contained in said gel slab platform;

a second buffer reservoir located adjacent a second end of said gel slab platform is adapted to maintain a second buffer solution in effective electrical contact with a second end of the gel slab contained in said gel slab platform, whereby an electrical potential may be applied across the gel slab contained within said gel slab platform;

a cooling unit for passing a cooling medium through said first flow channel and said second flow channel to cool the gel slab within said gel slab platform; and a plurality of dampers disposed in at least one of said flow channels for controlling the flow of said cooling medium through said flow channels formed in said apparatus.

21. The electrophoresis apparatus of claim 20, wherein the flow of said cooling medium is varied.

22. A gel slab electrophoresis apparatus, comprising:

a substantially vertical gel slab platform having a front panel and a back panel and containing therebetween a gel slab, wherein a first flow channel is formed between said front panel and the gel slab and a second flow channel is formed between the gel slab and the back panel of said apparatus;

a first buffer reservoir located adjacent a first end of said gel slab platform is adapted to maintain a first buffer solution in effective electrical contact with a first end of the gel slab contained in said gel slab platform;

a second buffer reservoir located adjacent a second end of said gel slab platform is adapted to maintain a second buffer solution in effective electrical contact with a second end of the gel slab contained in said gel slab platform whereby an electrical potential may be applied across the gel slab contained within said gel slab platform; and a cooling unit for passing a cooling medium through said first flow channel and said second flow channel to cool the gel slab within said gel slab platform;

wherein the apparatus is constructed so that the flow of said cooling medium through at least one of said first flow channel and said second flow channel is selectively variable across said gel slab.

* * * * *